(12) United States Patent
Bernardi et al.

(10) Patent No.: US 6,447,438 B1
(45) Date of Patent: Sep. 10, 2002

(54) APPARATUS AND METHOD FOR LOCATING THERAPEUTIC SEEDS IMPLANTED IN A HUMAN BODY

(75) Inventors: Richard Bruce Bernardi, Wayne, PA (US); Christopher John Vecchio, Philadelphia, PA (US)

(73) Assignee: Spectrasonics Imaging, Inc., Wayne, PA (US)

( * ) Notice: Subject to any disclaimer, the term of this patent is extended or adjusted under 35 U.S.C. 154(b) by 0 days.

(21) Appl. No.: 09/543,272

(22) Filed: Apr. 5, 2000

(51) Int. Cl.⁷ .................................................. A61N 5/00
(52) U.S. Cl. ................................ 600/3; 600/8; 128/899
(58) Field of Search ................................ 600/1–8, 443, 600/420, 424, 431; 128/899

(56) References Cited

U.S. PATENT DOCUMENTS

| 4,373,532 A | 2/1983 | Hill et al. |
| 4,510,924 A | 4/1985 | Gray |
| 5,161,536 A | 11/1992 | Vilkomerson et al. |
| 5,394,875 A | 3/1995 | Lewis et al. |
| 5,498,227 A | 3/1996 | Mawad |
| 5,713,828 A | 2/1998 | Coniglione |
| 5,931,786 A | 8/1999 | Whitmore, III et al. |
| 5,938,583 A | 8/1999 | Grimm |
| 5,961,527 A | 10/1999 | Whitmore, III et al. |

*Primary Examiner*—John P. Lacyk
(74) *Attorney, Agent, or Firm*—Ratner & Prestia

(57) ABSTRACT

Determining the locations of therapeutic seeds implanted in a body part by distinguishing the therapeutic seeds from the body part by imposing physical changes on the therapeutic seeds and sensing these physical changes in the therapeutic seeds. In one form of the invention, the therapeutic seeds are partially ferromagnetic and are caused to vibrate by a magnetic field and the vibrating therapeutic seeds are identified by reflections of ultrasonic signals transmitted to the therapeutic seeds.

10 Claims, 4 Drawing Sheets

APPARATUS AND METHOD FOR LOCATING THERAPEUTIC SEEDS IMPLANTED IN A HUMAN BODY

TECHNICAL FIELD

The present invention relates, in general, to dosimetry and therapeutic implants and, in particular, to an apparatus and method for determining the locations of brachytherapy seeds and other therapeutic seed implants.

BACKGROUND OF THE INVENTION

Ionizing radiation is used medically in a wide range of therapeutic procedures and treatments. Brachytherapy techniques, involving the implantation of radioactive "seeds" in a defined array, often are used to deliver controlled doses of radiation to specific regions and parts of the body. Typically, a diseased organ or other to structure, such as a tumor, is the target of the applied radiation. For example, in the treatment of prostate cancer, a prescribed number of radioactive seeds that serve to deliver controlled doses of radiation to the prostate are implanted at desired locations in the prostate.

Generally, it is desirable, and in many instances it is mandatory, to restrict the exposure to radiation to pathological regions and to minimize the effect of radiation on surrounding healthy structures. Treatment planning techniques that specify a three-dimensional matrix of radioactive seed implant placements attempt to achieve this result.

Due to difficulties and limitations in the ability of the attending physician to position the therapeutic seeds at the desired locations, the actual matrix of therapeutic seeds might be different from the one that is intended. As a result, the surrounding tissue can be is exposed to undesired amounts of radiation, while portions of the targeted pathological tissues might be underexposed and not receive the desired degree of radiation.

It is common practice to view the therapeutic seed implantations with CT or MRI equipment after the implantations have been completed to confirm that the therapeutic seeds have been positioned properly. Such a viewing of the implanted therapeutic seeds is very expensive and time consuming. When improperly implanted seeds are detected, corrections are made by implanting additional seeds at the desired locations, thereby subjecting the patient to another implantation procedure. This, of course, is undesirable because the implantation procedure is uncomfortable for the patient and exposes the patient to the risks associated with any such medical procedure.

Ultrasonic imaging often is used in conjunction with radiotherapy to locate target tissue structures and guide the therapy procedure. With brachytherapy, real-time ultrasonic images are used to guide the placement of the radioactive therapeutic seeds. Once the matrix of implanted seeds is in place, however, it is difficult to determine the locations of the implanted seeds because of acoustic reflections, shadowing and trauma-induced increases in tissue echogenesis. Consequently, it is still necessary to confirm, with CT or MRI equipment after the implantations have been completed, that the implanted seeds have been positioned properly.

SUMMARY OF THE INVENTION

Apparatus for determining the locations of therapeutic seeds implanted in a body part, constructed in accordance with the present invention, includes means for causing each of the implanted seeds to undergo a physical change that can be sensed and sensing means for detecting the physical changes of the implanted seeds and developing signals representative of the physical changes of the implanted seeds. Such apparatus, constructed in accordance with the present invention, also includes indicating means responsive to the signals developed by the sensing means for developing indications of the locations of the implanted seeds.

A method for implanting therapeutic seeds in a body part, conducted in accordance with the present invention, includes the steps of establishing desired locations in a body part for the implantation of a plurality of therapeutic seeds and implanting the plurality of therapeutic seeds in the body part. Also included in this method are the steps of causing each of the therapeutic seeds to undergo a physical change and identifying the therapeutic seeds by sensing the physical changes in the therapeutic seeds. This method further includes the steps of determining the locations of the therapeutic seeds from the identifications of the therapeutic seeds, comparing the determined locations of the therapeutic seeds with the desired locations of the therapeutic seeds and correcting the locations of those therapeutic seeds that are not implanted at the desired locations.

It is to be understood that both the foregoing general description of the present invention and the following detailed description of the present invention are exemplary, but are not restrictive, of the present invention.

BRIEF DESCRIPTION OF THE DRAWINGS

The present invention is best understood from the following detailed description when read in connection with the accompanying drawings. Included in the drawings are the following figures:

FIG. 2 shows a transrectal ultrasound imaging probe inserted in the rectum, a seed insertion trocar for implanting brachytherapy seeds into the prostate, and a template in proximity to the perineum for defining the locations of the seed implantations.

DETAILED DESCRIPTION OF THE INVENTION

The present invention will be described in connection with the implantation of brachytherapy seeds in the prostate to treat prostate cancer. It will be apparent that the present invention has broader application and can be employed for determining the locations of therapeutic seeds implanted in a body part for other purposes.

Figure 1:
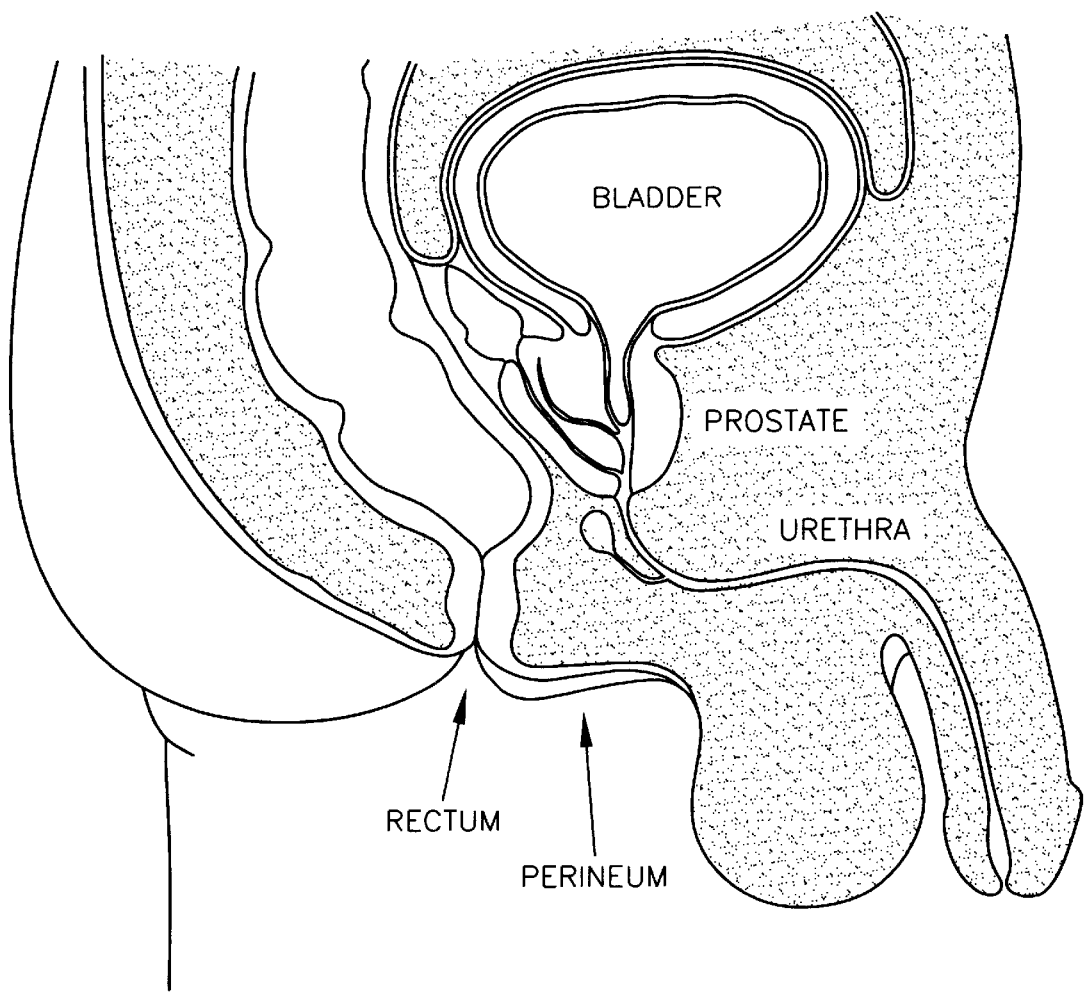
FIG. 1 illustrates the prostate and the neighboring anatomy of a human body.

Referring to FIG. 1, the prostate and neighboring anatomy of a human body are illustrated. Among the other body parts that are of particular importance and significance in describing and understanding the apparatus and method of the present invention are the rectum and the perineum.

Figure 2:
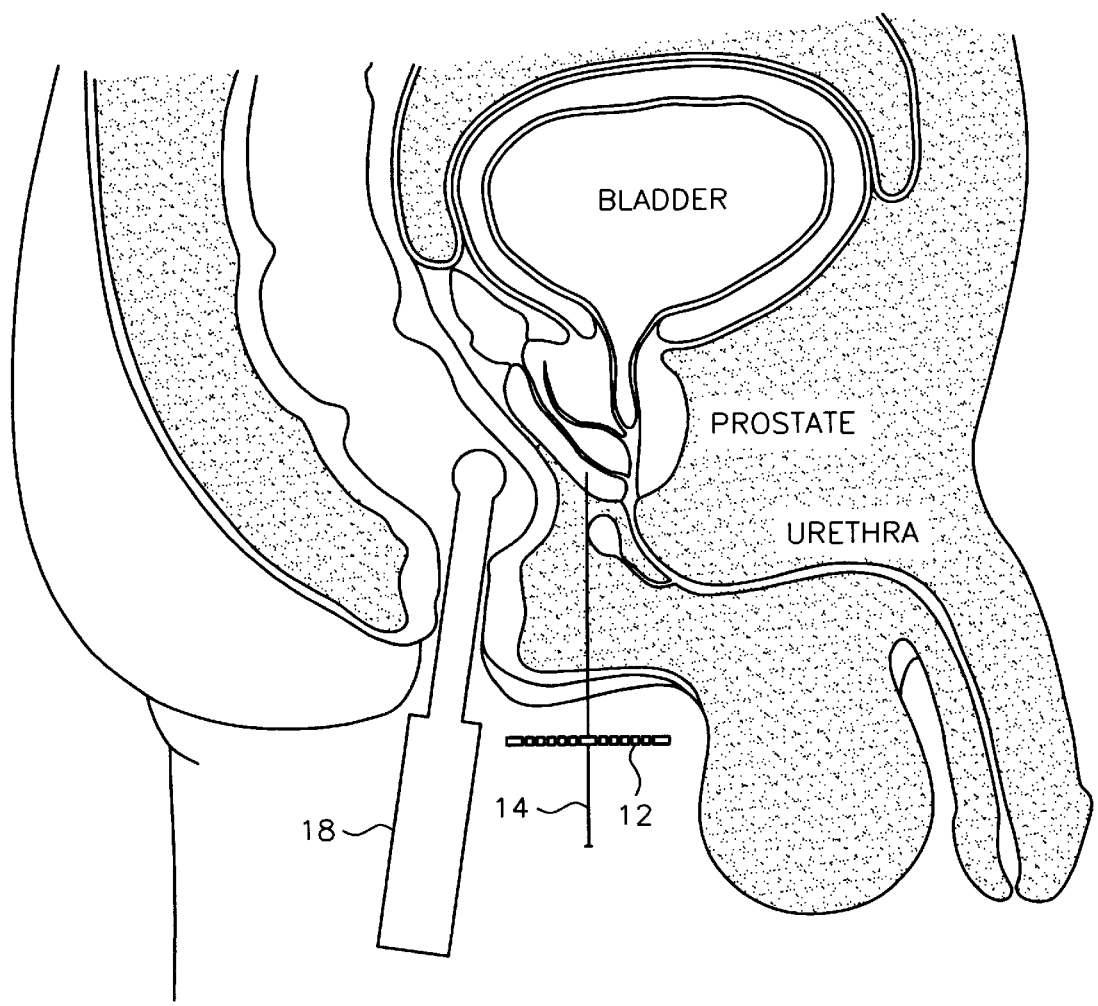
FIG. 2 is similar to FIG. 1, except
Figure 3:
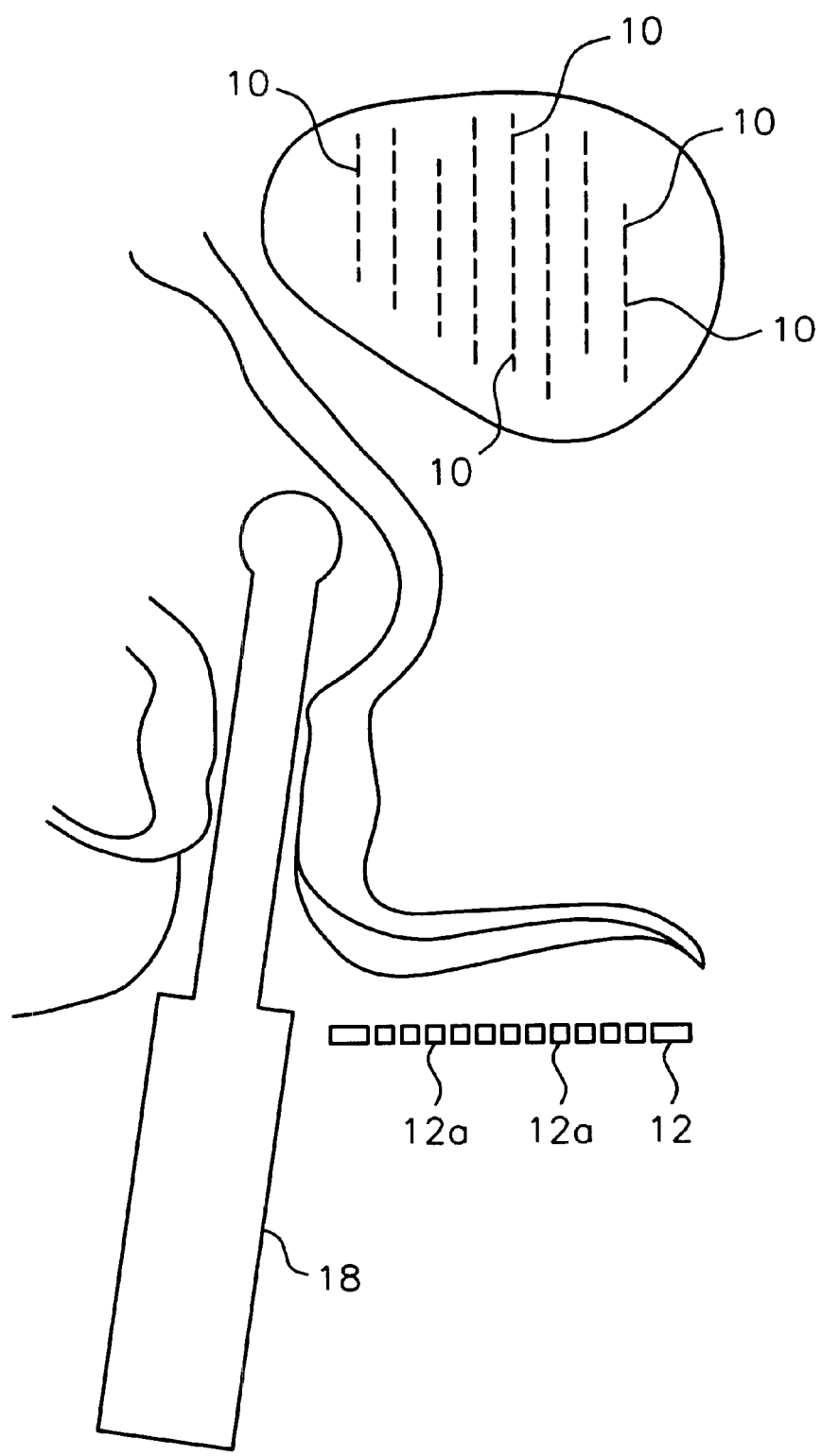
FIG. 3 is a simplified illustration of FIG. 2, but on a slightly enlarged scale, showing the transrectal ultrasound imaging probe, the template, and the prostate containing a matrix of brachytherapy seeds.

Referring to FIGS. 2 and 3, a method for implanting therapeutic seeds, namely radioactive seeds 10, in a body part, namely the prostate, in accordance with the present invention includes establishing desired locations in the prostate for the implantation of a plurality of radioactive seeds at points as close as possible to the target locations and then implanting the radioactive seeds at the established locations. Implantation of the radioactive seeds is accomplished, in part, by using a template 12, placed in proximity to the perineum, by which a seed insertion trocar 14 is aligned with the desired seed implantation locations in the prostate.

Template 12 has a two-dimensional array of guide holes 12a. Trocar 14, of conventional construction and operation, is passed through guide holes 12a, one at a time, and then through the perineum to the prostate to implant radioactive seeds 10 in the prostate in the usual manner.

As indicated above, when brachytherapy real-time ultrasonic images are used to guide the implantation of radioactive seeds 10, once the matrix of implants is in place, it is difficult to determine the seed locations because of acoustic reflections, shadowing and trauma-induced increases in tissue echogenesis.

In accordance with the present invention, radioactive seeds 10 implanted in the prostate are caused to undergo a physical change, so that when imaged, the implanted radioactive seeds can be distinguished from the neighboring anatomy. A preferred physical change of radioactive seeds 10 is a change in the disposition of the radioactive seeds.

By making radioactive seeds 10 slightly or partially ferromagnetic and applying a changing magnetic field that passes through the prostate, the implanted radioactive seeds are caused to vibrate in place, thereby changing the disposition of the radioactive seeds. When the area of the body is imaged, for example by ultrasonic imaging equipment, the moving (i.e. vibrating) radioactive seeds 10 are distinguishable from the neighboring anatomy. The magnetic field, shown in FIG. 4, can be developed by an induction coil 16 located externally of the body or the induction coil can be carried in an ultrasonic probe 18 inserted into the body through the rectum as illustrated by FIGS. 2 and 3.

In accordance with the present invention, radioactive seeds 10 are identified by sensing the physical changes in the radioactive seeds and then the locations of the radioactive seeds are determined from the identifications of the therapeutic seeds. In accordance with a preferred embodiment of the present invention, the vibrating radioactive seeds 10 can be sensed by an ultrasonic probe 18 by which an image of the prostate is developed showing the vibrating radioactive seeds.

The attending physician, by viewing the image, can compare the determined locations of radioactive seeds 10, as shown by the image, with the desired locations of the radioactive seeds and, if necessary, correct for improper locations of those radioactive seeds that have not been implanted at the desired locations. Such correction typically involves implanting additional radioactive seeds at the desired locations without removal of the improperly located radioactive seeds or removal of improperly located radioactive seeds when, for example, the radioactive seeds have been implanted improperly in the bladder.

Figure 4:
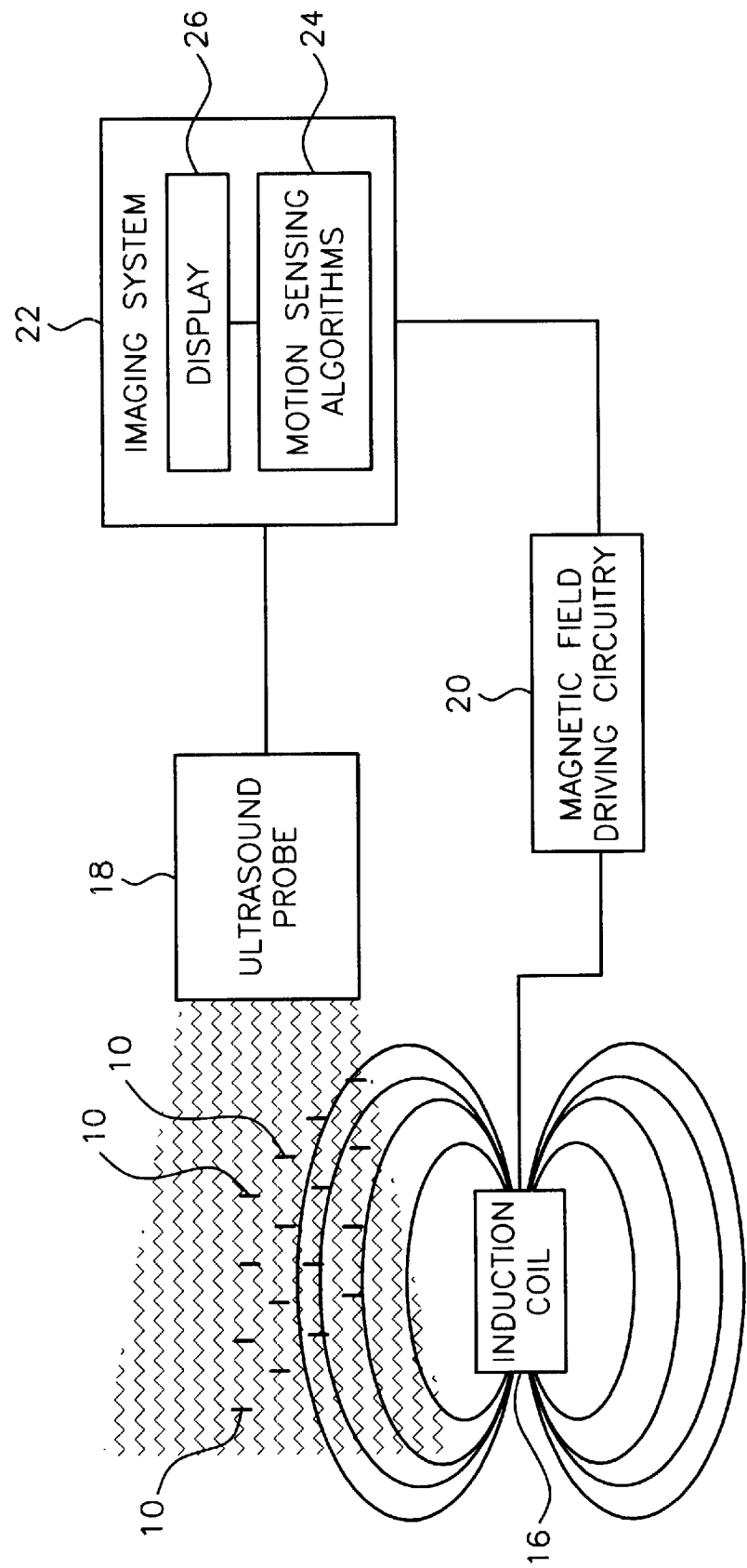
FIG. 4 is a block diagram of apparatus for determining the locations of therapeutic seeds implanted in a body part constructed in accordance with the present invention

Referring to FIG. 4, apparatus for determining the locations of therapeutic seeds implanted in a body part, constructed in accordance with the present invention, includes means for causing each of the implanted radioactive seeds 10 to undergo a physical change that can be sensed. For the embodiment of the invention being described, the means for causing each of the implanted seeds to undergo a physical change include means for changing the physical disposition of the implanted seeds, namely means for establishing a changing magnetic field that extends through the body part, namely the prostate, and causes the implanted seeds to vibrate. As shown in FIG. 4, an induction coil 16, to which current is supplied from magnetic field driving circuitry 20, creates a changing magnetic field that extends through the prostate in which radioactive seeds 10 have been implanted and causes the radioactive seeds to vibrate.

Apparatus for determining the locations of therapeutic seeds implanted in a body part, constructed in accordance with the present invention, also includes sensing means for detecting the physical changes of the implanted seeds and developing signals representative of the physical changes of the implanted seeds. For the embodiment of the invention being described, the sensing means include means for detecting vibrations of the implanted seeds by transmitting, in the usual manner, ultrasonic signals from an ultrasound probe 18 to the implanted radioactive seeds 10 and receiving, in the usual manner, reflections of the ultrasonic signals from the implanted radioactive seeds by the ultrasound probe. The physical changes of radioactive seeds 10, namely that the radioactive seeds are vibrating, are detected by ultrasound probe 18 which, in turn, develops signals, in the usual manner, representative of the physical changes of the radioactive seeds. In other words, ultrasound probe 18, operating in the usual manner, develops signals representative of what is being viewed, including the vibrating radioactive seeds.

Apparatus for determining the locations of therapeutic seeds implanted in a body part, constructed in accordance with the present invention, further includes indicating means responsive to the signals developed by ultrasound probe 18 for developing indications of the locations of the implanted radioactive seeds 10. As shown in FIG. 4, for the embodiment of the invention being described, the indicating means include an imaging system 22 that include means, such as motion sensing algorithms 24, for processing the signals developed by ultrasound probe 18 that are representative of the reflections of the ultrasonic signals and a display 26 responsive to the processed signals. Display 26 indicates the locations of radioactive seeds 10 in the same way that other views inside the body are displayed. A hardware implementation of the function performed by motion sensing algorithms 24 is a matched filter.

Motion sensing algorithms 24 or a hardware equivalent process the signals developed by ultrasonic probe 18 according to the nature and character of the current that is supplied from magnetic field driving circuitry 20 to create the changing magnetic field that causes radioactive seeds 10 to vibrate. Preferably, both the rate at which the magnetic field changes (i.e., frequency) and the manner in which the magnetic field changes (i.e., wave shape of applied current, such as sinusoidal, triangular, square, etc.) are factors that are included in the motion sensing algorithms 24 or a hardware equivalent to assure that the signals developed by ultrasonic probe 18, in response to the vibrating radioactive seeds 10, are distinguishable from other signals developed from the movements of other parts.

Although illustrated and described above with reference to a certain specific embodiment, the present invention is nevertheless not intended to be limited to the details shown. Rather, various modifications may be made in the details within the scope and range of equivalents of the claims and without from the spirit of the invention.

What is claimed:

1. Apparatus for determining the locations of therapeutic seeds implanted in a body part comprising:

means for causing each of the implanted seeds to undergo a physical change that can be sensed;

sensing means for:
(a) detecting the physical changes of the implanted seeds, and
(b) developing signals representative of the physical changes of the implanted seeds; and indicating means responsive to the signals developed by said sensing means for developing indications of the locations of the implanted seeds.

2. Apparatus according to claim 1 wherein said means for causing each of the implanted seeds to undergo a physical change include means for changing the physical disposition of the implanted seeds.

3. Apparatus according to claim 2 wherein:
(a) said means for causing each of the implanted seeds to undergo a physical change include means for establishing a changing magnetic field that extends through the body part and causes the implanted seeds to vibrate, and
(b) said sensing means include means for detecting vibrations of the implanted seeds.

4. Apparatus according to claim 2 wherein:
(a) said sensing means include:
(1) means for transmitting ultrasonic signals to the implanted seeds, and
(2) means for receiving reflections of the ultrasonic signals from the implanted seeds, and
(b) said indicating means include:
(1) means for processing the reflections of the ultrasonic signals, and
(2) a display responsive to the processed reflections of the ultrasonic signals.

5. Apparatus according to claim 3 wherein:
(a) said sensing means include:
(1) means for transmitting ultrasonic signals to the implanted seed, and
(2) means for receiving reflections of the ultrasonic signals from the implanted seeds, and
(b) said indicating means include:
(1) means for processing the reflections of the ultrasonic signals, and
(2) a display responsive to the processed reflections of the ultrasonic signals.

6. Apparatus according to claim 5 wherein said means for processing the reflections of the ultrasonic signals process the reflections of the ultrasonic signals according to the nature and character of the current that develops the changing magnetic field.

7. Apparatus according to claim 6 wherein the nature and character of the current that develops the changing magnetic field include the frequency and wave shape of the current.

8. A method for implanting therapeutic seeds in a body part comprising the steps of:

establishing desired locations in a body part for the implantation of a plurality of therapeutic seeds;

implanting said plurality of therapeutic seeds in the body part;

causing each of said therapeutic seeds to undergo a physical change;

identifying said therapeutic seeds by sensing the physical changes in said therapeutic seeds;

determining the locations of said therapeutic seeds from the identifications of said therapeutic seeds;

comparing the determined locations of said therapeutic seeds with the desired locations of said therapeutic seeds; and correcting the locations of those therapeutic seeds that are not implanted at the desired locations.

9. A method according to claim 6 wherein the physical change of said therapeutic seeds is a change in disposition.

10. A method according to claim 7 wherein said therapeutic seeds are at least partially ferromagnetic and the disposition of said therapeutic seeds is changed by applying a changing magnetic field.

* * * * *